United States Patent [19]

Baratta

[11] Patent Number: 5,052,819
[45] Date of Patent: Oct. 1, 1991

[54] METHOD OF AND APPARATUS FOR NONDESTRUCTIVELY DETERMINING THE COMPOSITION OF AN UNKNOWN MATERIAL SAMPLE

[76] Inventor: Francis I. Baratta, 138 Ridge St., Arlington, Mass. 02174

[21] Appl. No.: 364,462

[22] Filed: Jun. 12, 1989

[51] Int. Cl.[5] ............................................ G01N 25/00
[52] U.S. Cl. .......................................... 374/43; 374/12
[58] Field of Search ........................ 374/45, 43, 10, 12

[56] References Cited

U.S. PATENT DOCUMENTS 3,981,175  1/1976  Hammond, III et al. ............ 374/10

Primary Examiner—Daniel M. Yasich
Attorney, Agent, or Firm—J. D. Marshall

[57] ABSTRACT

This invention presents an improved way to determine, nondestructively, the composition of an unknown material sample such as, for example, a steel fastener of unknown standard grade. The procedure involves subjecting one end of a standard grade steel fastener of known length and weight to a pulse of heat and subjecting an identically-sized fastener of unknown grade to the equivalent or same conditions for an interval of time for the same finite length and comparing the time varying temperature pattern at the same heated ends of each fastener. The temperature of said locations can be monitored during the time heat is applied.

4 Claims, 3 Drawing Sheets

METHOD OF AND APPARATUS FOR NONDESTRUCTIVELY DETERMINING THE COMPOSITION OF AN UNKNOWN MATERIAL SAMPLE

FIELD OF THE INVENTION

The present invention relates to the nondestructive determination of the composition of a material when comparing the thermal properties of a sample of the material with the thermal properties of a standard of the same material, said standard having a desired composition.

The invention herein described has use for nondestructive qualitative determination of composition of a variety of materials and its use is discussed mostly with reference to counterfeit, mismarked, and substandard externally threaded steel fasteners.

BACKGROUND OF THE INVENTION

The recent influx of counterfeit threaded fasteners into the American economy has caused a multiplicity of problems, according to a report by the Subcommittee on Oversight and Investigations of the Committee on Energy and Commerce, U.S. House of Representatives. Unscrupulous manufacturers, importers and venders have distributed and sold over thirty millions of substandard fasteners in place of standard fasteners. The U.S. industries in the main utilize a standard for steel fasteners published by the Society of Automotive Engineers (SAE), SAE J 429 January 80. (Although this specification refers to the SAE J 429 Standard and cites particular grades of fasteners as examples, it is equally applicable to other fastener standards). As examples, lower grades 8.2 and 5.2 fasteners have been unknowingly bought by dealers and users in place of the higher grades 8 and 5 fasteners, respectively. Many of the lower grade fasteners have been falsely coded with the counterfeit grade identification markings.

The major differences between Grades 8 and 8.2 and 5 and 5.2 fasteners, as specified by SAE J 429 January 80, are in the percent permissible carbon and boron content. The Grades 8 and 5 contain higher amounts of carbon and therefore are of higher quality than Grades 8.2 and 5.2, respectively. Thus, additions of boron to Grades 8 and 5 steels, for the purpose of hardening, is unnecessary. The lower grade steel fasteners, Grade 8.2 and 5.2, have almost identical mechanical properties as the higher grade steel fasteners at ambient temperatures. However, following a high temperature excursion, the lower grade steel fasteners are susceptible to high temperature embrittlement, a condition that has led to catastrophic failures.

An additional difference between the Grade 8 and Grade 8.2 fastener is their heat treatments. Each, however, will conform to the required minimum mechanical properties at room temperature but not at elevated temperature since the Grade 8.2 fastener is of different composition and is tempered at a lower temperature than the Grade 8 fastener. The surface hardness of each grade is almost identical and not amenable to discrimination by hardness testing. Thus, destructively testing by tensile tests above the tempering temperature of the Grade 8.2 fastener is required to definitively determine the grade of each fastener.

Although both grades of fasteners are used at ambient temperature, the Grade 8.2 fastener will prematurely fail, compared to the Grade 8 fastener, due either to its greater susceptibility to stress corrosion cracking or hydrogen embrittlement.

Heretofore, the difference between the higher quality and lower quality fastener grades has been impossible to successfully detect in an accurate manner except by the costly destructive test method already mentioned and defined in SAE J 429 January 80. Thus, it is important that some way be found to detect the bogus fasteners, a way that avoids the usual destructive testing, a way that is nondestructive, fast, simple and accurate. Such a detection method is needed that will stop the illegal sale of bogus fasteners and detect those already invoiced so that they can be sorted and separated from higher grade fasteners and allow each grade to be appropriately classified for future use.

There are several methods of nondestructively discriminating between bodies having similar appearances but of slightly different composition or even of different material. The following paragraphs discuss appropriate examples of these.

In one instance the relatively old technology of eddy current testing technique is utilized to attempt to separate higher grade fasteners from lower grade fasteners. This method principally compares the electrical conductivity, synonymous with thermal conductivity, and magnetic permeability of a resulting read-out wave form of the higher grade standard fastener to that of the sample.

According to SAE J 490C, the standard permissible variations in alloy content between Grade 8 and Grade 8.2 fasteners result in a very small percent difference by weight in the alloying elements. The minimum differences allowed in carbon (C) and iron (Fe) content by percent weight between Grade 8 and Grade 8.2 fasteners, dictated by SAE J 490C. are 0.43 C and 0.28 Fe. Such small differences in these major alloying elements that affect the conductivity and the permeability of the fasteners, result in an estimated difference (by a linear mixture approximation) in thermal conductivity between Grade 8 and Grade 8.2 fasteners of only 0.2%. This difference is very small and out of the sensitivity range of the eddy current technique.

In another instance U.S. Pat. No. 4,255,962, issued to Leland E. Ashman, teaches a method of distinguishing a simulated diamond from a natural diamond by utilizing a probe which applies a pulse of heat to the surface of the sample in an air environment and during the occurance of thermal equilibrium the same probe detects the change in temperature. This change in temperature is related to the thermal conductivity of the sample. Since the thermal conductivity of natural diamond is at least an order of magnitude greater than a simulated diamond, such as cubic zirconia, it is readily detected. This method, however, is not sensitive enough to detect the slight change in thermal conductivity between Grade 8 and Grade 8.2 fasteners.

Another method of identifying materials nondestructively is disclosed in U.S. Pat. No. 2,924,771 issued to Elmer H. Greenberg et al. This invention teaches an improvement in the employment of the thermoelectric effect to identify a specimen of material and in particular metallic materials. This method utilizes a pair of electrically connected metallic contact members engaged with a sample specimen, wherein one contact member, the probe, provides the hot junction and at a lightly different region the other contact provides the cold junction. Thus, a thermoelectric voltage reading is generated which is claimed to identify the material.

The disadvantages of the above mentioned test method are numerous, with the major ones listed by the following comments:

a. Reproducibility of the reading is dependent upon the relative thermal conductivity and diffusivity of the probe and sample, as well as a properly proportioned probe geometry and contact area; and use of proper probe metal. In addition, resharpening of the probe with use is necessary.

b. Means have to be provided to minimize variable radiation losses in the contact members, otherwise the test becomes highly inaccurate. This necessitates calibration and control of additional heat to the system by the operator.

c. Optimum sensitivity is attained for different metals by previous tests of known specimens. Certain readings may be indicative of two or more metals. The ambiguity may be resolved by a single probe test wherein such results are then compared to a listing for that probe and may in all probability identify the specimen, if the diffusivities and thermoelectric effects are not too close.

d. Resultling test readings must be compared to a table of materials, each of known chemical analysis and physical condition when read with this method of standardization.

It is obvious from the noted disadvantages associated with the method described in U.S. Pat. No. 2,924,771, that it is not operator simple, reproducibility and accuracy is dependent upon a priori knowledge of the sample material, and results may well be ambiguous, such that the sample could not be definitively identified.

Another example of a nondestructive test method is described in U.S. Pat. No. 3,981,175, which was issued to Ogden H. Hammond III and Francis I. Baratta (hereby expressly incorporated by reference). In accordance with that system, the device is a nondestructive counterfeit gold bar and silver bar detection system based upon heat transfer principles. The principle entails the application of identical finite suddenly applied controlled heat pulses at a first region of a gold or silver bar of known purity, used as a standard, and the test bar of the same dimensions. The system is enclosed in an insulating medium. The temperatures are measured at a second region of each bar, which are not only dependent upon the thermal properties of each bar, but upon the time. Specifically, those thermal properties which are tested by this devise are specific heat, thermal conductivity, and density; and the combination of these properties known as diffusivity. Since these properties in gold and silver are unique, the temperature at the second region, specifically the end opposite from that which is suddenly pulsed by a quantity of heat will be at a higher temperature in a given time than that of any bar less pure than the standard gold or silver bar. Because of the large differences in thermal properties of gold and an alloyed gold sample, temperature measurements will reveal differences. However, the thermal properties of Grade 8 and 8.2 bolts are very similar and temperature determinations at their far ends will not guarantee discrimination.

Yet another example of a nondestructive test method to detect fraudulent precious metal bars is revealed in U.S. Pat. No. 4,381,154, issued to Ogden H. Hammond, III. It was found that of all possible forgeries, a nonalloyed tungsten forgery of gold, i.e., an insert of tungsten within the gold bar, is the most difficult to detect because the density and heat-capacity of tungsten and gold are virtually identical (a less difficult forgery to detect is an alloyed forgery wherein its composition is generally uniform throughout). Thus, an improvement in accuracy over the previous U.S. Pat. No. 3,981,175 was required. This improvement consists mainly of increasing the accuracy of the detection system by providing and controlling heat into the test chamber resulting in equilibrium, termed dynamic insulation; accurate heater control and using a compensated infrared sensor to measure the temperature at the far end opposite the heated end of the sample.

Although the improved techniques adopted in U.S. Pat. No. 4,381,154 will enhance the sensitivity of this test method it requires additional temperature sensors, controls and electronic instrumentation as compared to the method prescribed in U.S. Pat. No. 3,981,175.

Because the thermal properties of ferrous materials are not as unique as gold or silver, simple improvements of U.S. Pat. No. 3,981,175 are required to nondestructively detect counterfeit, mismarked, and substandard steel fasteners in a viable manner.

SUMMARY OF THE INVENTION

The objects of the present invention are to provide improvements for the nondestructive comparison of the composition of an unknown material sample to the composition of a known material sample and provide a mechanism for such a nondestructive comparison determination, and one that can be operated by persons with only a small amount of technical training.

Still another object is to provide such a mechanism for the nondestructive determination of the composition of steel fasteners of known length and known weight.

Still another object is to provide the foregoing mechanism for the nondestructive determination of the composition of steel samples in the form of fasteners and to give alarm in the event that a particular fastener fails to meet a standard.

Another object is to provide a characteristic temperature versus time curve or characteristic signature for higher grade standard fastener sizes against which the sample fastener sizes are to be compared.

The foregoing objects are achieved, broadly, in a method of determining nondestructively the composition of an unknown grade of fastener by noting the thermal characteristics of the sample and matching or comparing said thermal characteristics with the thermal characteristics of a standard fastener of the same general type material and of known composition. The method includes controllably applying heat to the sample at a region to provide a time-varying temperature pattern in the sample, measuring the temperature of the same region thereof and comparing the time-varying temperature of pattern of the standard subjected to equivalent conditions for the same length of time.

The teaching of U.S. Pat. No. 3,981,175 and U.S. Pat. No. 4,381,154 applied a heat pulse at a first region and measured the temperature of the second region exclusively at the farthest end of the standard and sample, opposite of the first region. The improved invention described herein allows for the temperature measurements at the ends at which the pulses of heat are applied to the standard and the sample. In this way, a comparison of temperature differences between the standard and fastener definitively reveals the temperature differences such that the Grade 8.2 fastener can be sorted from the Grade 8 fastener. However, if the temperature differences were measured at the far ends of the standard fastener and the sample fastener, as prescribed in U.S. Pat. No. 3,981,175 and U.S. Pat. No. 4,381,154, comparisons would show that the test would not always be able to separate Grade 8.2 fasteners from Grade 8 fasteners.

BRIEF DESCRIPTION OF THE DRAWINGS

Other and further objects, advantages and features of the invention will be apparent to those skilled in the art from the following detailed description thereof, taken in conjuction with the accompanying drawings, in which.

DESCRIPTION OF THE PREFERRED EMBODIMENTS

In the description that now follows, the invention is first discussed with reference to a system for determining nondestructively the composition of an unknown sample in rod form and, to simplify the explanation, the sample taken up is a steel fastener, but it will be kept in mind that most aspects of the system discussed with respect to steel fasteners may also apply to other materials not having unique thermal properties as those of gold or silver.

Figure 1:
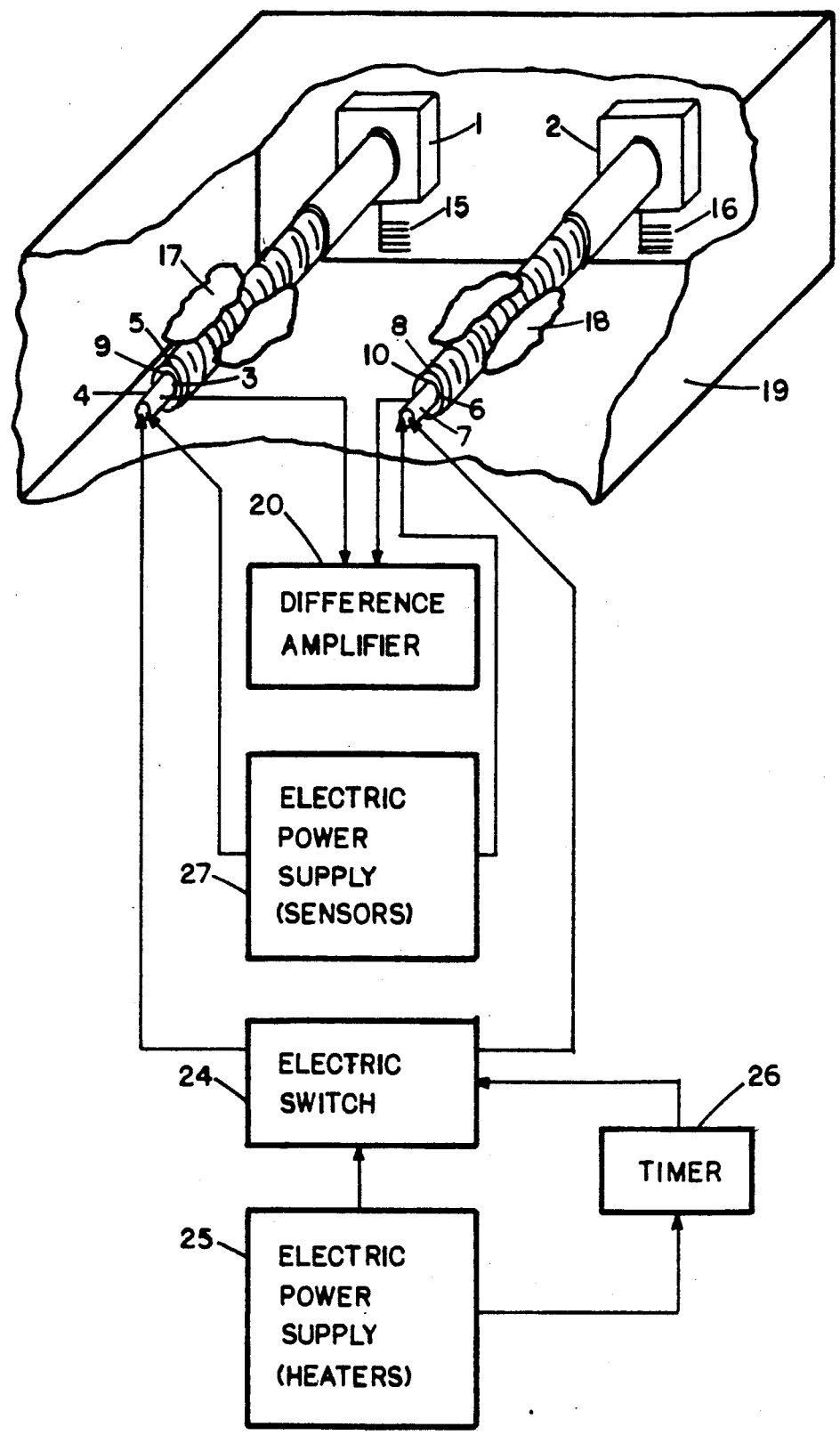
FIG. 1 is a diagrammatic representation, partly block diagram in form and with portions of the apparatus shown being partly cutaway, of a system adapted to effect nondestructive determination of the composition of a material sample.

Turning now to FIG. 1, the apparatus shows, for such non-destructive determination, a solid elongate sample or fastener 1 of unknown precise composition which is compared with a solid elongate standard or fastener 2 of known composition, as now explained. An electric-resistance heater 3 in housing 4 applies heat to the sample 1 at an end 5 thereof and, at the same time, an electric resistance heater 6 in housing 7 applies heat to the standard 2 at an end 8 thereof, thereby to provide time-varying temperature patterns in the sample and the standard. Simultanously, with or at a predetermined time after the heat is applied and for a predetermined time interval, the temperatures or time-varying temperature patterns of the sample, and the standard are sensed or noted and compared. The sensing functions are provided by transducer 9 in housing 4 and transducer 10 in housing 7, both operatively disposed to sense the time-varying temperatures at ends 5 and 8, respectively of the sample and the standard, thus providing as output an electrical signal that is a function of the time-varying temperature. Note each pair of heater means and temperature sensor means making contact with a fastener are well insulated from each other. The two electrical signals are connected as inputs to a difference amplifier 20 which notes any difference between the two electrical signals due to a temperature differential and amplifies the same.

Figure 2:
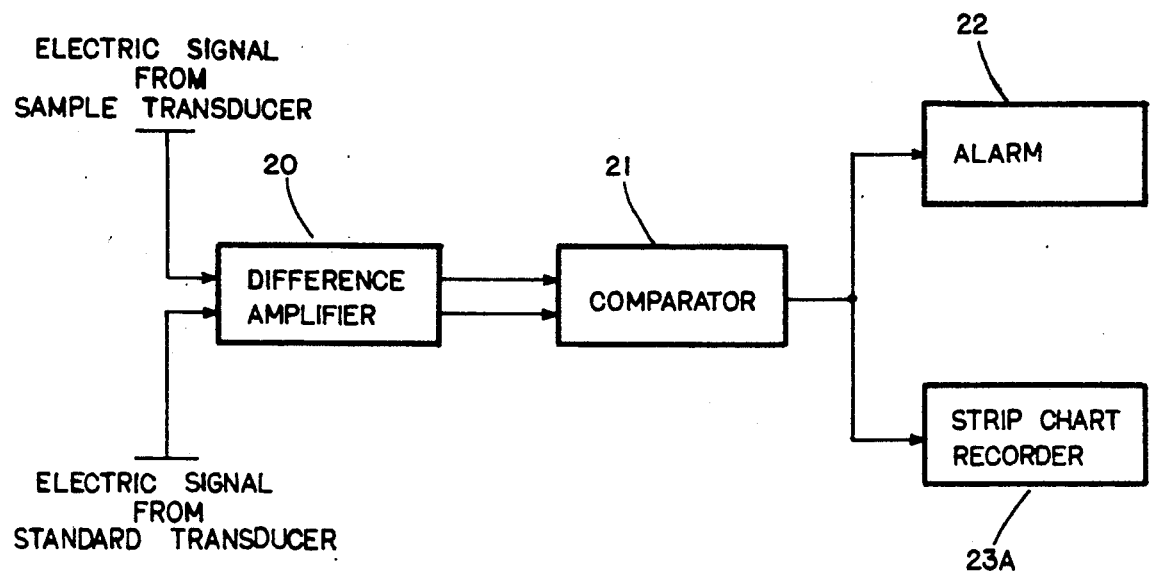
FIG. 2 shows in block diagram form a part of the system of FIG. 1 but slightly modified.

In FIG. 2, a comparator 21 is connected to receive an output from the difference amplifier 20 and is connected to an alarm 22 which is activated in those instances in which the alloying content of sample 1 varies from that of the standard 2, or to a recorder 23A. To complete the electric circuitry of FIG. 1 by which sample composition is evaluated or analyzed, the heaters 3 and 6 are electrically energized through a switch 24 from an electrical power source 25. The sequencing and timing of the events in the system is provided by a timer means 26.

In the apparatus shown by FIG. 1, the heating elements 3 and 6 contact one end of the unknown fastener sample and the standard fastener, respectively, as noted above. The length and weight of each fastener must be known. This can be readily accomplished through exterior means or done through sensors built into the testing apparatus (this is not shown in FIG. 1 so as to retain clarity). At the heated ends of the fasteners, locations 9 and 10, are transducers, powered if required by an electrical power source 27, to determine the temperature at said location of each fastener and, most important, to determine the relative changes in temperature in some time pattern which will give rise to a temperature difference.

The fasteners, heaters, and temperature sensing devices should be well insulated from the environment, but good thermal contact is essential between the fasteners and the heating elements and the fasteners and the temperature sensing devices. (In order to insure good thermal contact the sample and the fastener will have to be finished machined with the same slight spherical radius at their threaded ends.) Axial forces are provided to maintain such contact by leaf or other light springs 15 and 16 that are insulated, thermally and electrically from the fasteners. Each fastener, heating element, and temperature sensor should be well insulated from each other and the other fastener, heating element, and temperature sensor. (In FIG. 1 the fasteners 1 and 2 are separated from one another, and thermal insulating material 17 and 18 is placed around and between the fasteners. In the actual apparatus the housing labeled 19 within which the fasteners are placed has an insulating recess to receive each fastener). Each heater means should be of a type that provides controlled heat input as opposed to a constant temperature source; the heat thus applied is a controlled amount; and the resistances 3 and 6 for acceptable results must have low heat capacity so that most of the heat generated therein is transferred to the associated fasteners 1 and 2. Heaters found to be best are those that provide a concentrated amount of heat in a small area. If heat (e.g., a square wave pulse of indefinate duration) is applied to one end of a fastener at $x=L$, the general equation for the temperature at any distance x (assuming the fastener to be well insulated) is given by the expression:

$$T(x) = \frac{QL}{k} \left\{ \frac{at}{L^2} + \frac{3x^2 - L^2}{6L^2} - \frac{2}{\pi^2} \sum_{m=1}^{\infty} \frac{(-1)^m}{m^2} [\exp(-am^2\pi^2 t/L)]\cos(m\pi a/L) \right\} \quad (1)$$

where:
Q is the suddenly applied constant heat flux per unit area (BTU/sec-ft$^2$) at $x=L$,
L is length in feet,
k is the thermal conductivity BTU/sec-ft-°F.,
$a$ is the thermal diffusivity in ft/sec$=k/\rho$ c,
$\rho$ is the density in lbs/ft, c is the specific heat BTU/lb-°F.,
t is time in seconds, x is the distance along the bar (note at
x=0 there is no flow of heat), and
T(x) is temperature in °F.
(See Carslaw and Jeager "Conduction of Heat in Solids," Oxford Press, 1950, page 104, paragraph 43, eq. (1)). If the temperature is measured at x=L, at the same end at which heat is applied equation 1 becomes:

$$T = \frac{QL}{k}\left\{\frac{\alpha t}{L^2} + \frac{1}{3} - \frac{2}{\pi^2}\sum_{m=1}^{\infty}\frac{(-1)^m}{m^2}[\exp(-\alpha m^2\pi^2 t/L)]\cos(m\pi)\right\} \quad (1A)$$

If an attempt is made to counterfeit a fastener, the weight W in pounds and the length in feet, would be dependent upon its size. Thus, equation (1A) becomes:

$$T = \frac{q}{W}\left\{\frac{t}{c} + \frac{\rho}{3k} - \frac{2L^2\rho}{\pi^2 k}\sum_{m=1}^{\infty}\frac{(-1)^m}{m^2}[\exp(-\alpha m^2\pi^2 t/L)]\cos(m\pi)\right\} \quad (2)$$

where:

q is the suddenly applied contant heat flux in BTUs/sec and all other terms are as defined above.

The predominant factors in equation (2) that control the temperature as a function of time of each fastener are the first term and the series summation. The higher grade fastener always has a higher thermal diffusivity than the lower grade fastener. Thus, it develops that if the time period of testing is correctly selected for a given bolt size, the higher grade fastener will attain a higher temperature than the lower grade fastener at their ends at which $\chi=L$ (the heated ends).

Thus, it is sufficient that at all times during the test interval, the temperature at the heated end of the suspected counterfeit fastener be as high as that of the known fastener (or a recording thereof). For certainty if the fastener in question has the same alloying elements and within the prescribed minimum and maximum limits as the higher grade fastener, as given in SAE J 429 January 80 and SAE J 490C, then it will be as hot or hotter as the higher grade fastener used as a standard for comparison. (Note that the maximum limit of percent alloying elements and the mimimum percent of iron are used as the higher Grade 8 standard for comparison and thus the fastener in question if it is Grade 8.2 will be lower in temperature than the standard for comparison). This is subject to several restrictions and possible errors which are taken up in the next paragraph.

Figure 3:
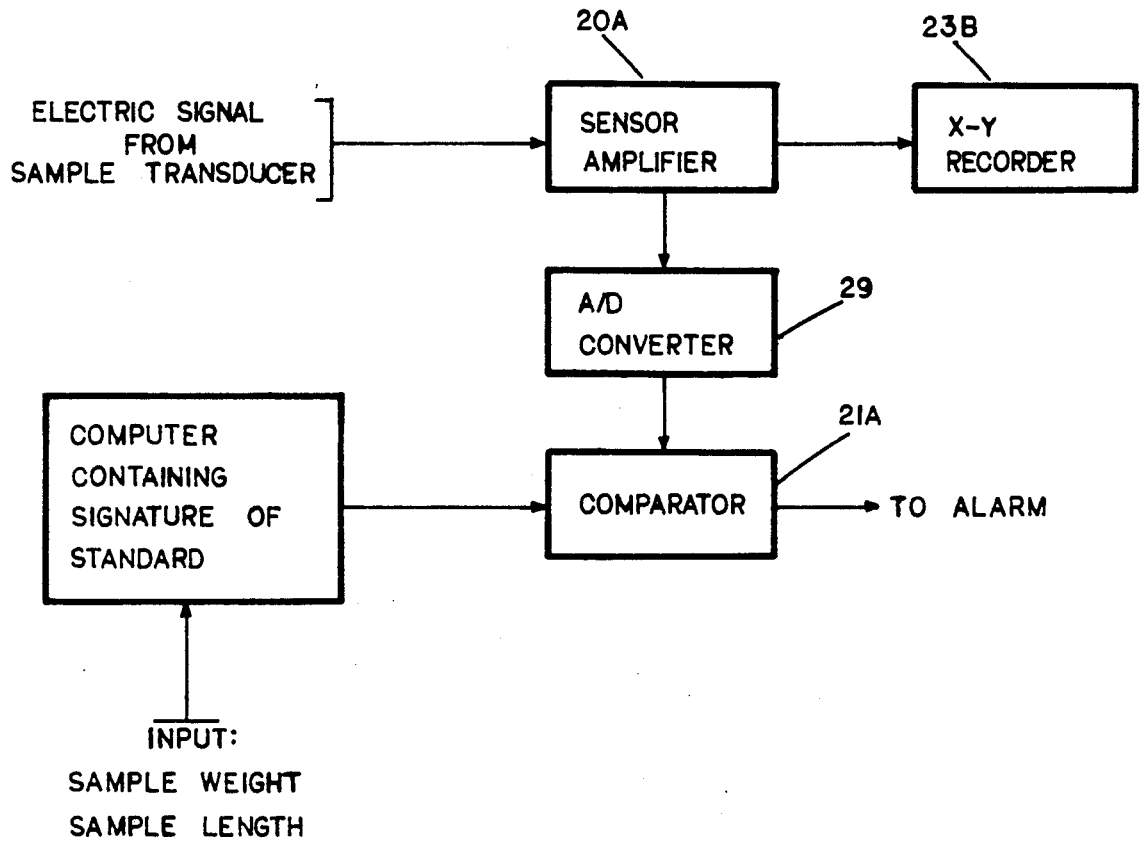
FIG. 3 shows in block diagram form another modified version of a part of the system of FIG. 1.

The ratio $q_{sa}/W_{sa}=q_{st}/W_{st}$ (wherein $q_{sa}$ and $q_{st}$ are the heat inputs to the sample and standard of respective weights $W_{sa}$ and $W_{st}$) must be kept within acceptable tolerance. The test is as good as the exactitude with which the lengths and weights are known. It may be impracticable to match lengths and weights of the test sample fastener and the standard fastener for comparison. However, it is not necessary that the standard actually be present at the time the sample is tested. Thus, in FIG. 3 the time-varying patterns of a sample fastener, converted to electric signals as before, are fed to a sensor amplifier 20A and thence to an analog-to-digital converter 29, the output of the converter being connected as one input to a comparator 21A, the other input to which is from a computer allows the measured length and weight of the sample fastener, and has stored the signatures of an equivalent standard. Note the measurement of length and weight can be integral to the test device (for simplicity this is not shown in FIG. 1) and automatically programmed into the computer as shown in FIG. 3, or be manually programmed. The output of the comparator 21A can connect to an alarm. Also, the sensor output can be connected as outputs to an X-Y recorder 23B.

The device shown in FIG. 1 displays only one sample and standard fastener. However, means for accomodating several sizes and utilize the same computer for all sizes can readily be accomplished.

Figure 4:
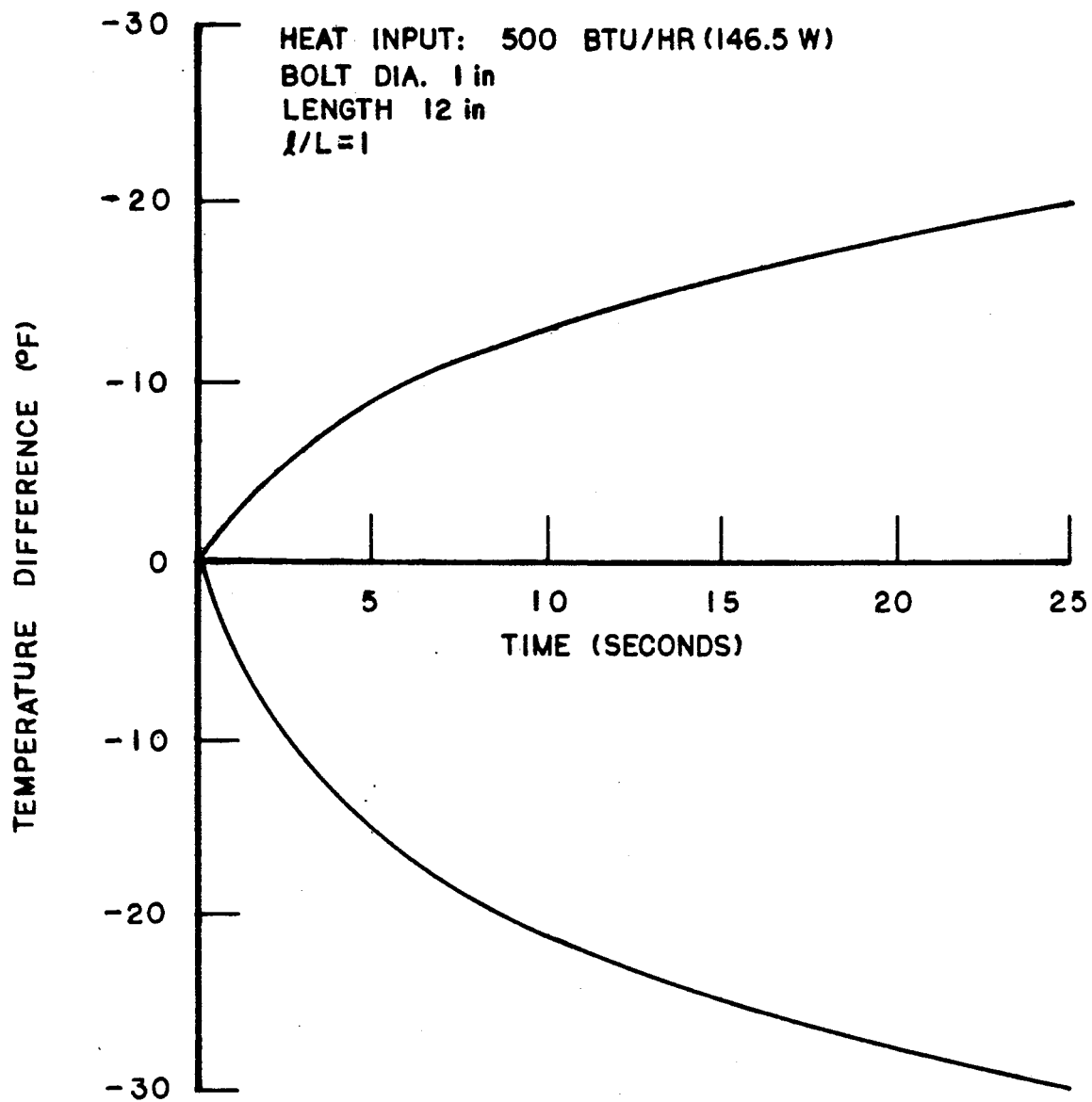
FIG. 4 is a graphical representation of temperature differences as a function of time measured at the heated ends of a standard and test sample of a particular size of steel fastener.
Figure 4:
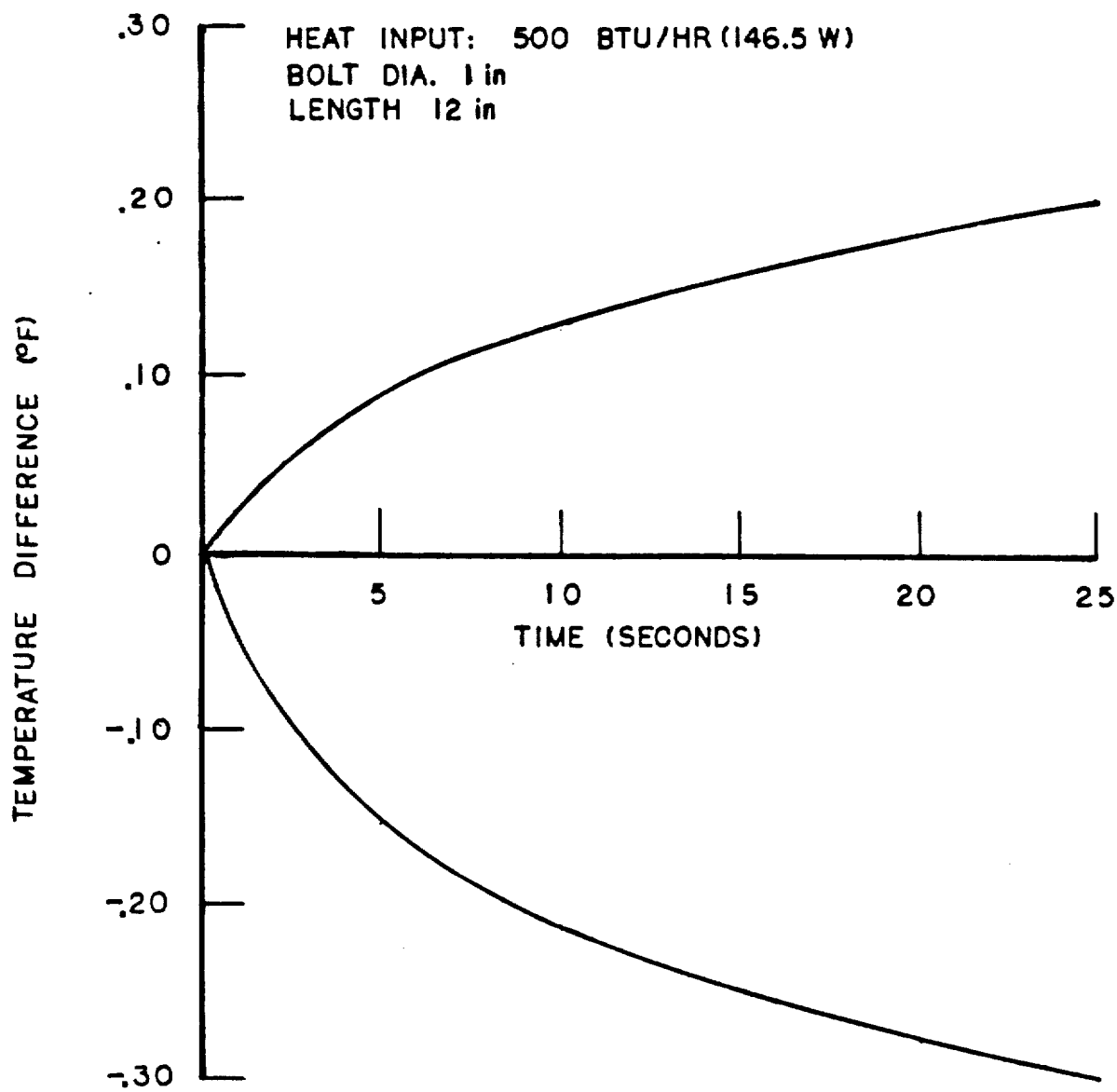

As mentioned previously, the invention is an improvement to U.S. Pat. No. 3,981,175 which prescribed applying a heat pulse at the first region and measuring the temperature at a second region (exclusively at the far end of the sample) at some time interval. The improvement described herein requires measuring temperatures of the sample fastener at its end where the heat pulse is applied, but again at some time interval as put forth in the aforementioned patent. As an example of this improvement consider FIG. 4, which describes typical temperature difference - time curves for a Grade 8 fastener (the standard for comparison) 1 inch in diameter by 12 inches long and a Grade 8.2 fastener (the sample to be tested) of the same size; each experiencing a heat input of 500 BTU/hr (146.5 Watts). In order to demonstrate the feasibility of the test method the chemical compositions of the Grade 8 fastener (the standard) and the Grade 8.2 fastener (the test sample) were chosen to be as close to each other as possible within the limits prescribed in SAE J 429 January 80 and SAE J 490C. Shown in this figure are curves A and B, the results of these computations based on equation 2. Presented in FIG. 4 are the temperature differences Δ T in degrees Farenheit between the standard and test sample as a function of time at $\chi=L$ as measured at their heated ends. Curve A shows a positive temperature difference between the standard Grade 8 fastener which yields the lowest temperature-time curve amongst all Grade 8 fasteners, and the grade 8.2 fastener, which yields the highest temperature-time curve amongst all Grade 8.2 fasteners. Curve B shows a negative temperature difference between the aforementioned Grade 8 fastener used as a standard and a Grade 8 fastener that yields the highest temperature curve amongst all Grade 8 fasteners.

Thus, it is seen that in the above circumstances, a Grade 8.2 fastener will always be cooler at the prescribed temperature location, which is its heated end, and prescribed time interval than the standard when each are subjected to the same conditions. Also, if the test sample is indeed of higher grade it will test either equivalent in temperature or higher than the standard used for comparison and thus indicate a differential temperature of zero or less. This can readily be indicated by the alarm 22 shown in FIG. 2 as a go-no-go indication.

Notice that the temperature differences shown in FIG. 4 are great enough to be readily measured even for the large fastener size chosen as an example but still aining temperatures at the heated ends of the fasteners well below their specified heat treatment temperatures so as not to change their mechanical properties.

The apparatus herein described provides fast, foolproof and economical determination of composition, and thermal properties of samples in a system which avoids the high skill needed for such determination by observing surface properties, the multiple tests of chemical analysis, and destruction of the fastener (see SAE J 429 January 80). It makes possible such analysis by unskilled persons in a go-no-go type mode of operation. In the case of many materials, and in particular ferrous fasteners, it makes possible improved testing and checking of samples, compared to U.S. Pat. No. 3,981,175 for which no such procedure was presented, and if it had it would not be successful. The accuracy of results is related to the size of the fastener and the prescribed time interval of testing, as well as the quality of electronics employed.

Further modification of this improvement over the original invention herein disclosed will occur to persons skilled in the art and all such modifications are deemed to be within the spirit and scope of this invention as defined by the appended claims.

What is claimed is:

1. Apparatus for determining nondestructively the composition of an unknown sample that comprises, in combination: means for appying heat at a rate $q_{sa}$ at one end of an elongate sample of weight $W_{sa}$; means for simultaneously applying heat at a rate $q_{st}$ at one end of a standard of weight $W_{st}$ and having the same length as the length of the sample such that $q_{sa}/W_{sa}=q_{st}/W_{st}$; first transducer means positioned to sense the temperature at the heated said one end of the sample and to provide a first electric signal; second transducer means positioned to sense the temperature at the heated said one end of the standard located at substantially the same position as that of the sample and to provide a second electric signal; and means connected to receive and analyze the first electric signal and the second electric signal over time to determine the relative magnitudes, either qualitatively or quantitatively, of the temperatures at the said heated ends of the sample and of the standard.

2. Apparatus for determining nondestructively the composition of an unknown elongate sample that comprises, in combination: means for applying heat to the sample at one end of the sample; means for sensing the resulting time-varying temperature of the sample at the heated said one end of the sample; a known standard of the same length as the sample; means for applying heat to the standard at one end of the standard; means for sensing the resulting time-varying temperature of the standard at the heated said one end of the standard; and means for simultaneously comparing the time-varying temperature pattern for a predetermined finite length of time at said heated one end of the sample with the time-varying temperature pattern of the known standard of the same length subjected to equivalent conditions for the same finite length of time.

3. A method of determining nondestructively the composition of an unknown material sample, that comprises: applying heat at one end of an elongate sample of said material to provide a time-varying temperature pattern in the sample; controlling the rate of heat input to the sample; measuring the temperature as a function of time at the heated said one end of the sample; and simultaneously comparing the time-varying temperature pattern for a predetermined finite length of time at said heated one end of the sample with a time-varying temperature pattern of a known standard subjected to equivalent conditions for the same length of time, the sample and the standard being of the same length and being simultaneously subjected to heat input at a constant rate at each of their said one ends, the temperature of each being sensed at the heated said one end, and the temperature of the sample at the heated said one end thereof being compared to the temperature of the standard at the heated said one end thereof continuously and for a finite length of time.

4. A method of determining nondestructively whether an unknown elongate sample bar has at least the same composition as an elongate standard bar of material of known composition and of the same length as the length of the sample or varies in composition by an acceptable amount, that comprises: applying heat at one end of the sample bar to provide a time-varying temperature pattern in the sample; controlling the rate of the heat input to the sample; measuring the temperature as a function of time at the same said one end on said sample bar and comparing the time-varying temperature pattern for a predetermined finite length of time at said one end of the sample with the time-varying temperature pattern at a heated said one end of a known standard subjected to substantially the same heat input for substantially the same length of time to determine whether relative temperature changes of the sample are at all times at least as great at the heated said one end thereof as relative changes in temperature of the standard at the heated said one end thereof or said changes in temperature are lower than the changes in temperature of the standard at said heated one end of the standard by some acceptable predetermined small amount.

* * * * *

UNITED STATES PATENT AND TRADEMARK OFFICE
CERTIFICATE OF CORRECTION

PATENT NO. : 5,052,819
DATED : October 1, 1991
INVENTOR(S) : Francis I. Baratta

It is certified that error appears in the above-indentified patent and that said Letters Patent is hereby corrected as shown below:

Column 6, line 67, after the words "the thermal diffusivity in" delete [ $ft^2$/sec] replace with --$ft^2$/sec.

Column 6, line 68, after the word "in" delete [ lbs/ft] and replace with --lbs/$ft^3$.--

UNITED STATES PATENT AND TRADEMARK OFFICE
CERTIFICATE OF CORRECTION

PATENT NO.  : 5,052,819
DATED       : October 1, 1991
INVENTOR(S) : Francis I. Baratta It is certified that error appears in the above-indentified patent and that said Letters Patent is hereby corrected as shown below:

The drawing sheet consisting of Figure 4, should be deleted to be replaced with drawing sheet, consisting of Figrue 4 as shown on the attached page.

Signed and Sealed this

Fourteenth Day of June, 1994

BRUCE LFHMAN

Attest:

*Attesting Officer*        Commissioner of Patents and Trademarks